US010966815B1

(12) United States Patent
Kemper et al.

(10) Patent No.: US 10,966,815 B1
(45) Date of Patent: Apr. 6, 2021

(54) ENCLOSURE DEVICE FOR AN IMPLANTABLE REPAIR DEVICE

(71) Applicant: EMBODY, INC., Norfolk, VA (US)

(72) Inventors: Nathan Kemper, Norfolk, VA (US); Michael Francis, Norfolk, VA (US); Christy Nelson, Norfolk, VA (US); Yas Maghdouri-White, Norfolk, VA (US)

(73) Assignee: EMBODY INC., Norfolk, VA (US)

( * ) Notice: Subject to any disclaimer, the term of this patent is extended or adjusted under 35 U.S.C. 154(b) by 0 days.

(21) Appl. No.: 16/937,886

(22) Filed: Jul. 24, 2020

Related U.S. Application Data

(60) Provisional application No. 62/938,028, filed on Nov. 20, 2019.

(51) Int. Cl.
*A61F 2/00* (2006.01)
*A61F 2/08* (2006.01)

(52) U.S. Cl.
CPC .... *A61F 2/0805* (2013.01); *A61F 2250/0085* (2013.01)

(58) Field of Classification Search
CPC ............ A61F 2/0063; A61F 2250/0085; A61F 15/002; A61F 15/001; A61F 15/00; A61F 13/15747; A61F 2013/00902; A61F 2013/00897; A61F 13/00085; A61F 13/0008; A61F 13/00076; A61F 13/00072; A61F 2/0095; A61F 2/0805;
(Continued)

(56) References Cited

U.S. PATENT DOCUMENTS 4,496,045 A 1/1985 Ferguson
5,219,077 A * 6/1993 Transue ............... A61F 2/0063
206/438

(Continued)

FOREIGN PATENT DOCUMENTS

WO 2013/122568 A1 8/2013

OTHER PUBLICATIONS

International Search Report and Written Opinion of PCT International Application No. PCT/US2020/043381, dated Nov. 23, 2020.

*Primary Examiner* — Brian A Dukert
*Assistant Examiner* — Rebecca Lynee Zimmerman
(74) *Attorney, Agent, or Firm* — J.A. Lindeman & Co., PLLC

(57) ABSTRACT

An enclosure device is disclosed for delivering an implantable sheet-like support or repair device, such as ligament, tendon or other soft tissue support or repair device, to a surgical site. The enclosure device protects the support or repair device from unwanted adhesion and deformation during delivery and facilitates its optimal positioning at the injury or repair site where the support or repair device will be implanted. The enclosure device has a planar body foldable along one or more fold lines into at least two panels configured to contain the repair device between the panels; an optional cutout in one or more panels of the planar body at the panel edge opposite the fold line configured to expose a portion of the repair device; an optional positioning tab extending out from the fold line; and an optional securing mechanism to secure the enclosure device in a folded position. Methods of using the enclosure device are described.

23 Claims, 13 Drawing Sheets

(58) Field of Classification Search
CPC ....... A61F 2002/0072; A61M 2209/06; A61M 25/002; A61M 15/0043; A61M 5/002; A61M 1/167; A61L 2202/182; A61L 2202/181; B65D 75/20; B65D 75/14; A61B 17/04
See application file for complete search history.

(56) References Cited

U.S. PATENT DOCUMENTS

| | | | |
|---|---|---|---|
| 5,249,682 | A | 10/1993 | Transue |
| 8,790,413 | B2 | 7/2014 | Meulink |
| 8,821,585 | B2 | 9/2014 | Pfeiffer et al. |
| D719,443 | S | 12/2014 | Jones |
| 10,398,571 | B1 | 9/2019 | Clayton |
| 2004/0267276 | A1 | 12/2004 | Camino |
| 2007/0282160 | A1* | 12/2007 | Sheu ............... A61L 31/148 600/30 |
| 2011/0308983 | A1* | 12/2011 | Dacey ............... A61F 2/0095 206/438 |
| 2012/0217176 | A1 | 8/2012 | Dacey et al. |
| 2014/0025093 | A1 | 1/2014 | Horton et al. |
| 2016/0100926 | A1 | 4/2016 | Bayon et al. |
| 2017/0143551 | A1 | 5/2017 | Coleman |
| 2017/0181829 | A1 | 6/2017 | Felix et al. |
| 2018/0162619 | A1* | 6/2018 | Kocur ............... A61B 50/33 |
| 2019/0020928 | A1 | 1/2019 | Chan et al. |

* cited by examiner

ENCLOSURE DEVICE FOR AN IMPLANTABLE REPAIR DEVICE

CROSS-REFERENCE TO RELATED APPLICATIONS

This application claims priority to U.S. Provisional Patent Application No. 62/938,028 filed Nov. 20, 2019; which is incorporated herein by reference.

TECHNICAL FIELD

This invention relates to an enclosure device for delivering an implantable sheet-like support or repair scaffold, such as a soft tissue repair device, to a surgical site without deforming or tearing the sheet-like repair device. The invention also relates to a method for implanting a sheet-like support or repair device using such an enclosure device.

BACKGROUND

Tendons, ligaments and other soft tissue failures or injuries can contribute greatly to reduced productivity and quality of life. One therapeutic approach to repairing or replacing these soft tissues through tissue engineering uses implantable sheet-like repair devices to support and repair soft tissue injuries. These implantable devices are often made from natural and biocompatible polymers that promote healing of the tissue while providing structure and support to the site of injury. These implantable devices may be implanted and absorbed into the body over the time period in which native cells infiltrate the implant and/or the devices may exist for relatively longer periods of time as additional support.

Such implantable sheet-like repair devices greatly enhance healing of the soft tissues by promoting growth, may carry therapeutic agents to the surgical site, and reduce stress/strains to the soft tissues from everyday activities. Examples of such implantable soft tissue repair devices are found in US Patent Applications 2019/0054205 A1 and 2019/0134267 A1, the disclosures of which are incorporated in their entireties.

In some situations, a repair device is implanted without utilizing a protective delivery vehicle. For example, sutures attached at one edge of a sheet-like repair device may be used to draw the device into the body and into its predetermined position for attachment. See, for example, the instructions provided for arthroscopic implantation of the Graftiacket™ regenerative tissue matrix at www.wright.com/footandankleproducts/graftjacket (accessed Nov. 2, 2019).

In other situations, protecting a sheet-like repair device during implantation is desired. Such devices may be somewhat fragile and can also have flexible, sticky, and/or spongy material properties that may result in a difficult insertion in small openings and spaces without unwanted accidental deformation, tearing or adhesion; such as when a wrap is implanted around a damaged or torn Achille's tendon to support its surgical repair. Like that of a conventional plastic kitchen wrap, adhesion to itself may occur. In such event or where adhesion to unwanted tissues in the vicinity or a surgical site occurs, this may result in the need to either replace the implantable device and/or result in an increased amount of time during the surgical procedure to adjust placement of the implantable device.

Further, some implantable sheet-like repair devices may require a particular implantation orientation due to fibers of the sheet-like repair device being aligned or oriented in a particular direction. Such aligned sheet-like repair devices may enhance growth, reduce stress/strain, or have greater strength in the directional orientation of the fibers, and thus require an aligned implantation. For example, an aligned sheet-like repair device may be used in tendon repair to provide extra stress reduction and physical support along the length of the tendon, where the fibers of the device are aligned parallel to the length of the tendon.

Additionally, in some products, one side or face of the sheet-like repair device may include a nonadherent outer surface or barrier layer or the fibers on one face are substantially isotropic and on the other face are substantially anisotropic. Thus, the sheet-like repair device must also be oriented for implantation with a particular face toward, for example, a tendon or ligament or other tissue to be supported and repaired.

Other implantable sheet-like repair devices include unaligned components (e.g., fibers) that do not require an aligned implantation but for which protection during implantation is desirable. For example, an unaligned sheet-like repair device may be used as an overlay for hernia repair where the same strength is needed in every direction of the implanted unaligned sheet-like repair device.

The success and effectiveness of surgical procedures may partially be related to the size of opening of the surgical site and time left open (that is, reducing exposure to the interior of a subject's body). Thus, such unwanted deformation and/or adhesion results in unintended and undesirable effects, which either result in extended surgical time to replace an implantable sheet-like repair device due to adherence to the wrong tissues or itself, or result in larger surgical site openings due to more space being required for access to the site of injury.

Some types of implants are protected by a tapered sleeve or funnel through which an implant is introduced into a large proximal end of the sleeve and extruded into a surgical pocket through a small sized distal end of the device. See, for example, International Patent Application WO 2013/122568 A1, which describes a delivery system for silicone breast implants rather than a sheet-like repair device.

In other surgical approaches, a guiding device is used to facilitate the delivery and handling of a tissue repair device (or patch) during a repair procedure. For example, US Patent Application 2017/0143551 A1 describes a suture guided arthroscopic technique and related devices including a patch having multiple sleeves and a tube through which to pass a suture as well as a delivery tool that advances the patch along the sutures and through a delivery cannula. In an embodiment of this device, the delivery tool has hollow legs as separate channels for individual sutures that lead to individual suture anchors affixed to bone.

Other instruments for delivering implants include a longitudinal slide portion and spaced walls defining longitudinal channels. The slide instrument is positioned to deliver an implant at its distal end to a damaged tissue site. See, for example, US Patent Application 2004/0267276 A1.

There also are surgical dispensing packages, for example, U.S. Design Pat. No. D719,443, which discloses a foldable package for sutures having a front flap that folds down.

Thus, there is a need for a solution to reduce the possibility of unwanted effects while delivering and positioning an implantable sheet-like support or repair device at a surgical site, particularly those contemplated for use when the implanted device is to be wrapped around a damaged ligament or tendon or other soft tissue.

SUMMARY OF THE INVENTION

The invention provides an enclosure device and methods of its use to deliver, insert and position a sheet-like, implantable support or repair device, particularly a soft tissue support or repair device, for example, that is inserted into a subject for use to wrap around a damaged ligament or tendon or to overlay damaged tissue as in a repair for hernia periosteum, nerve sheathing, dura mater, cartilage repair, to deliver a product to wrap bone, or to apply a graft to other internal organs, such as for hemorrhage control or to use as an internal wound dressing among others. By providing an insertion and delivery or enclosure package for such implantable support or repair devices, surgical procedures benefit from having relatively little or no deformation or adhesion of the implantable support or repair device, reduced surgical and tissue exposure time and smaller incisions at the site of injury.

Accordingly, the invention relates to an enclosure device for delivering an sheet-like implantable support or repair device, such as a ligament or tendon support or repair device, to a surgical site, the enclosure device having a planar body foldable along one or more fold lines, preferably substantially parallel fold lines, into at least two panels configured to contain or enclose an implantable sheet-like support or repair device between the panels; an optional cutout in one or more panels of the planar body at the panel edge opposite the fold line configured to expose a portion of both sides of the implantable sheet-like repair device; an optional positioning mechanism proximate to the fold line; and an optional securing mechanism to secure the enclosure device in a folded position.

The invention also relates to an enclosure device of the invention having an implantable sheet-like support or repair device positioned between the at least two panels of the enclosure device.

The invention further relates to a method of delivering an implantable sheet-like support or repair device, particularly a ligament, tendon or other soft tissue support or repair device, to a surgical site using an enclosure device of the invention by positioning the enclosure device within the surgical site; separating the enclosure device from the support or repair device; and implanting the support or repair device at the surgical site.

In preferred embodiments of the invention, the soft tissue support or repair device is made from substantially pure collagen or from a mixture of collagen and a biocompatible polymer. Preferred biocompatible polymers include polylactic acid (PLA), poly(D-lactic acid)(PDLA), poly(D,L-lactic acid) (PDLLA), poly(lactic-co-glycolic acid) (PLGA), poly(glycolic acid) (PGA) and mixtures thereof.

In other embodiments of the invention, the enclosure device is made from a material such as Acetal, Polyurethane (PUR), Ultra-high-molecular-weight Polyethylene (UHMW-PE), Low-density Polyethylene (LDPE), High-density Polyethylene (HDPE), polylactic acid (PLA), Polyether ether ketone (PEEK), Polyethylene terephthalate (PET), Polytetrafluoroethylene (PTFE or "Teflon"), and Polyvinylidene fluoride (PVDF).

DETAILED DESCRIPTION OF THE INVENTION

The invention provides an enclosure device for delivering an implantable sheet-like support or repair device, such as a sheet-like, soft tissue support or repair device, and methods of use that simplify and make more efficient surgical procedures for repair, reconstruction, regeneration, and/or therapy of bodily tissues, including musculoskeletal and central nervous system tissues and organs, for example, injuries to fat, tendon, muscle, articular cartilage, nerves, fascia, intervertebral discs, synovium, joint capsules and blood vessels. Although exemplary embodiments of the invention may refer specifically to tendons and ligaments, the invention may be used for any number of surgical procedures for treatment of the bodily tissues with sheet-like, soft tissue repair devices. Two such embodiments of an enclosure device are discussed hereafter. The first including multiple securing mechanisms, and the second including a single securing mechanism.

Figure 1:
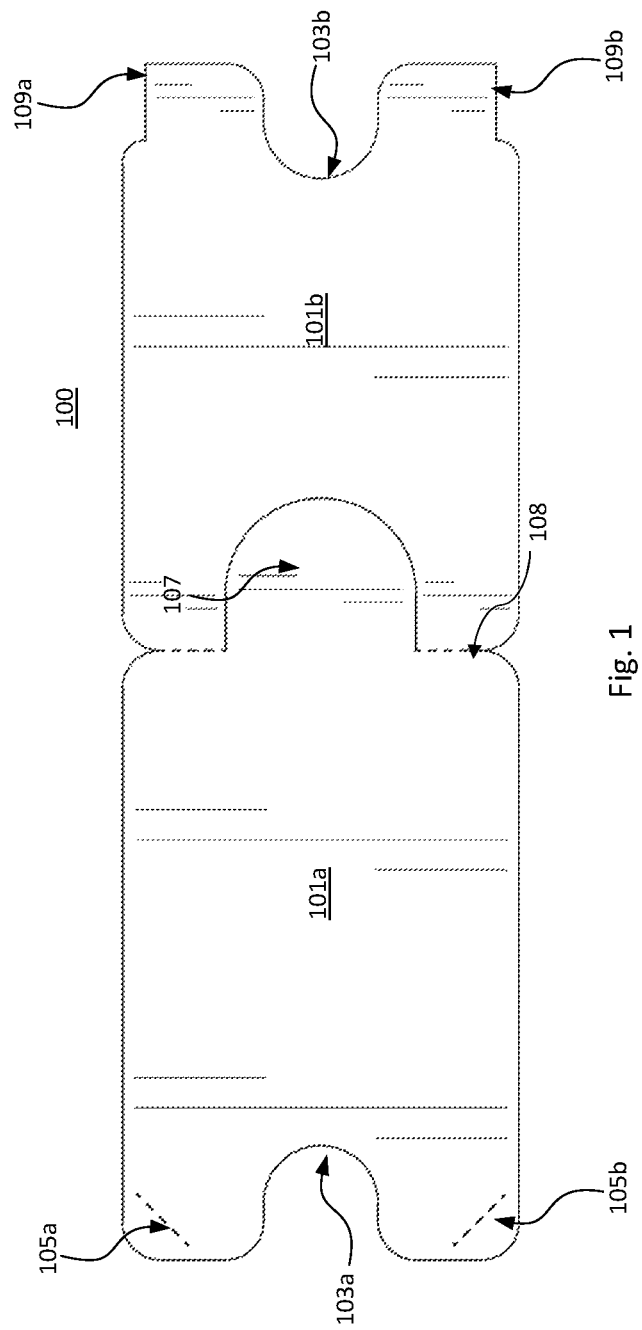
FIG. 1 is an exemplary illustration of an enclosure device of the invention for delivering an implantable sheet-like support or repair device, such as a ligament, tendon or other soft tissue support or repair device.

According to the invention, an enclosure device is provided for delivering an implantable sheet-like repair device to a surgical site. FIG. 1 shows an exemplary enclosure device 100 of the invention. The enclosure device 100 has a planar body foldable along a fold line 108 into two panels 101a, 101b configured to contain an implantable sheet-like repair device (not shown) between the panels 101a and 101b. An enclosure device of the invention has an optional cutout 103a and 103b in both panels 101a and 101b of the planar bodies at the panel edge opposite the tab configured to expose a portion of an implantable sheet-like repair device (not shown) within the enclosure device 100. The enclosure device may generally include dimensional lengths ranging between about 20 mm to about 200 mm, preferably ranging between about 40 mm to about 180 mm, or ranging between about 40 mm to about 170 mm. For example, one embodiment of an enclosure device of the invention, intended for use for Achilles tendon repair, may have dimensions of about 52 mm by about 80 mm when in a closed position and about 52 mm by about 161 mm in the open position. A person skilled in the art will be able to modify the size and dimension of the enclosure device consistent with the size of implant to be delivered to a subject.

An enclosure device of the invention may have an optional positioning mechanism 107 proximate to the fold line 108. An enclosure device of the invention may also have an optional securing mechanism to secure the enclosure device in a folded position.

In FIG. 1, the securing mechanism includes two slits 105*a* and 105*b* and two tabs 109*a* and 109*b* for securing the containment portion 101*b* to the body portion 101*a*. The slits 105*a* and 105*b* mate with and are complementary to tabs 109*a* and 109*b*.

Figure 2:
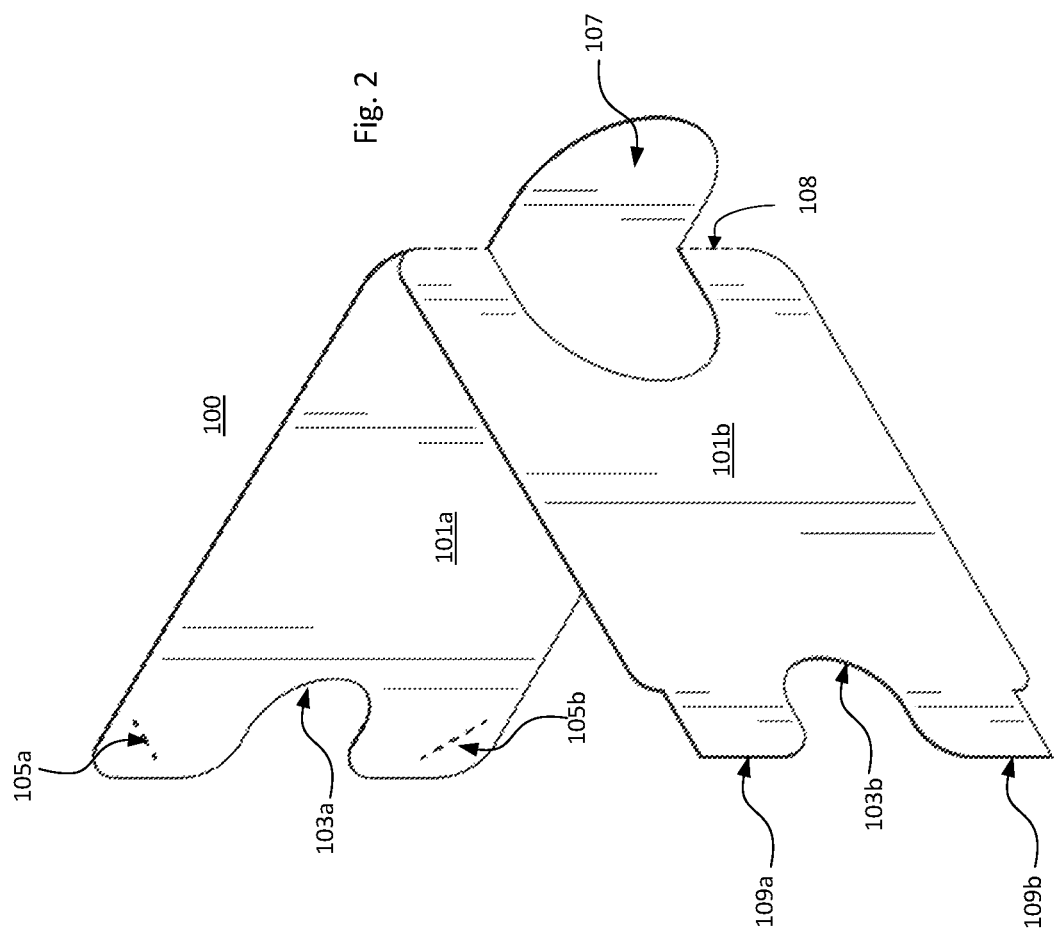
FIG. 2 is an exemplary illustration of the enclosure device of FIG. 1 for delivering an implantable sheet-like support or repair device in a partially folded state.

FIG. 2 depicts an enclosure device of the invention in a partially folded state. Although the enclosure device is depicted as folding in equal halves, the fold line 108 is not required to be at the center of the planar body and need only be located such that panels 101*a* and 101*b*, when folded, sufficiently capture an implantable sheet-like repair device allowing for its delivery to a surgical site.

The size and dimensions of an enclosure device, such as length, area, thickness, height of fold, etc. may be varied depending on the type and location of the surgical site and the nature of the implantable sheet-like repair device to be inserted, for example, when the enclosure device is used for implanting a relatively thicker repair device. Although not shown in FIGS. 1 and 2, the outer side of one of the panels 101*a* and 101*b* may include an imprint, coloration, cuts or other markings notifying the user, typically a surgeon, of the side of the enclosure device 100 that should be delivered facing and/or in contact with the body part being repaired, such as a tendon. For example, the imprint may read: "TENDON SIDE" to indicate a side of the enclosure device containing a sheet-like, soft tissue repair devices with particular surface materials or properties to be placed against or wrapped around the tendon undergoing repair.

An aligned sheet-like repair device may include, but is not limited to, an implantable sheet-like support or repair device manufactured by methods that may include electrospinning and pneumatospinning, or hybrid techniques thereof, which produce an implant with a gradient of alignment intended to be implanted with aligned fibers facing along the tendon and also having an opposite face with a randomly oriented backing. Other examples of aligned implantable sheet-like repair devices may include an allograft with different matrices on top and bottom (such as basal and laminal sides of dermis), or implantable sheet-like repair devices made by additive manufacturing (for example, 3D printed) having a particular directionality throughout the implant. Thus, due to orientation/alignment requirements of the repair devices, an associated enclosure device may have directionality such as front/back and up/down to maintain the critical orientation of the aligned sheet-like repair device for proper implantation.

Figure 3:
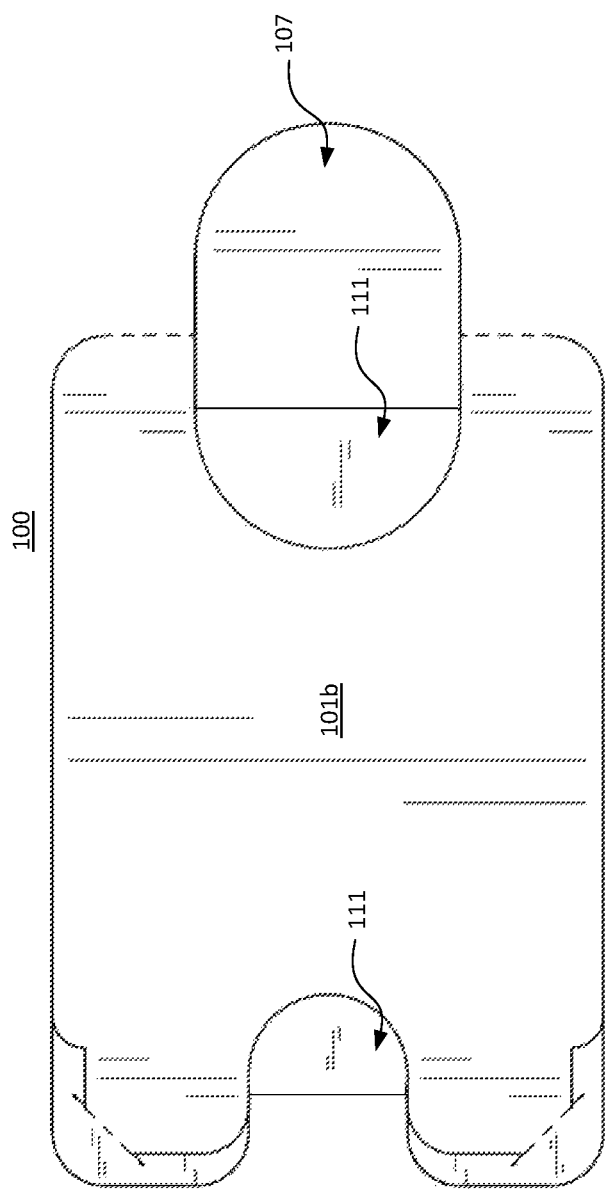
FIG. 3 shows an implantable sheet-like support or repair device, which is enclosed in the enclosure device of FIGS. 1 and 2.

An enclosure device for delivering an implantable sheet-like repair device to a surgical site may contain the sheet-like, tissue repair device. This allows an implantable sheet-like repair device to be pre-packaged for use in surgery. As shown in FIG. 3, such an enclosure device 100 has a planar body folded along a fold line into two panels configured to contain the sheet-like soft tissue repair device 111 between the panels. An implantable sheet-like repair device contained between the two panels. A cutout in one or both panels of the planar body at the panel edge opposite the fold may expose a portion of the repair device. As shown in FIG. 3 an enclosure also may have an optional positioning tab 107 extending out from the fold that can be used to pull the enclosure into the intended site at which the repair device is intended to be implanted. The enclosure also may have an optional securing mechanism to secure the enclosure device in a folded position.

Figure 4:
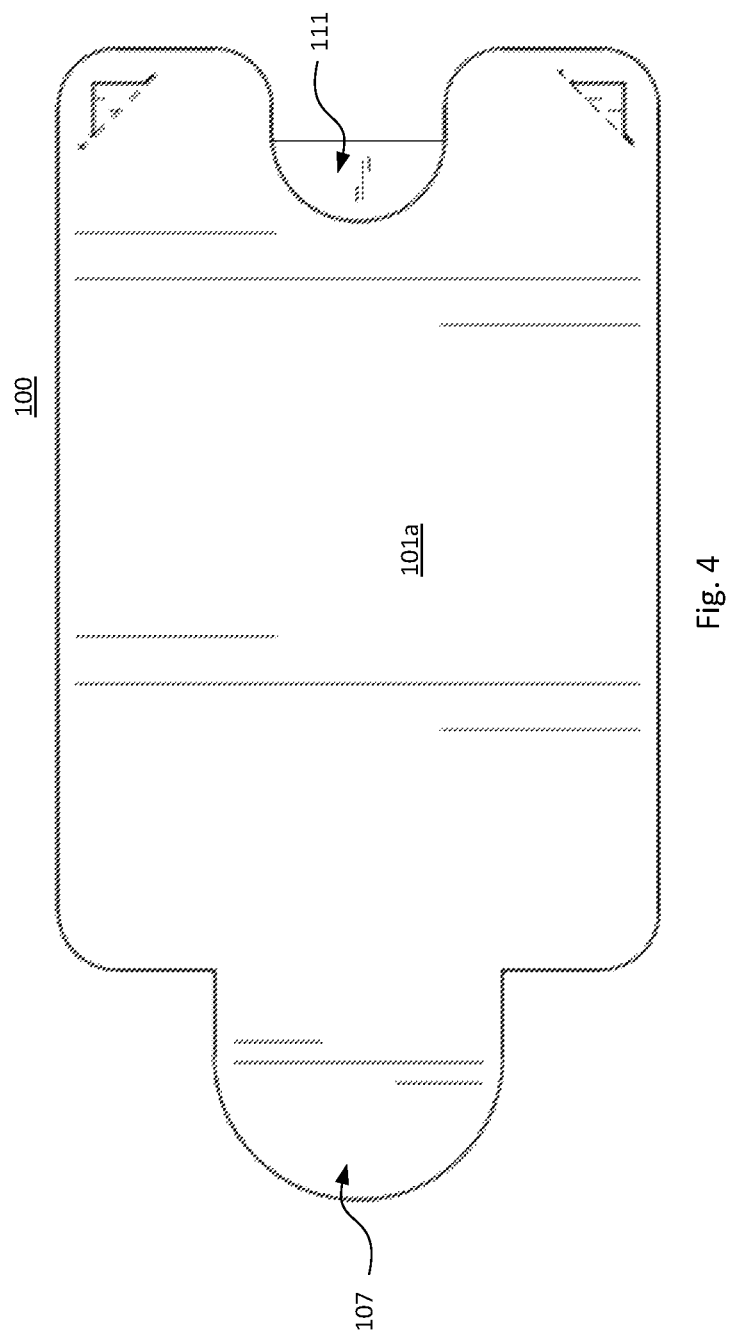
FIG. 4 is an exemplary illustration of a rear view of the enclosure device of FIGS. 1-3 in a fully folded and secured state.

As shown in FIG. 4 an enclosure using a mated slit and tab securing mechanism, when in a folded and secured position, will have the tab peeking through the panel 101*a* containing the slit.

Figure 5:
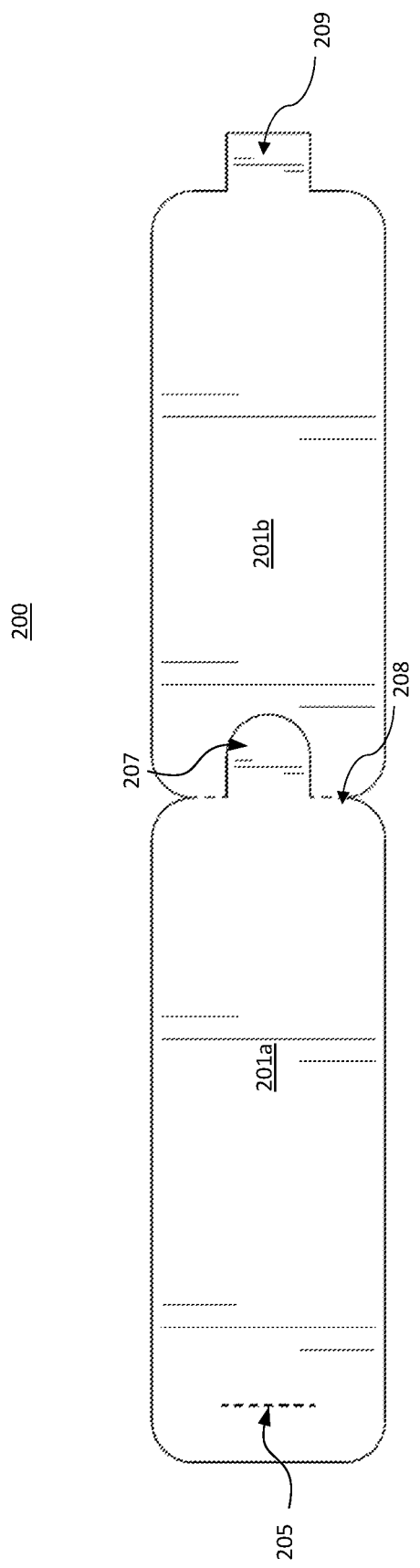
FIG. 5 is an exemplary illustration of another enclosure device of the invention for delivering an implantable sheet-like support or repair device.

FIG. 5 is an exemplary illustration of another enclosure device of the invention for delivering an implantable sheet-like repair device. In FIGS. 5-8, the securing mechanism includes a single slit 205 and tab 209 for securing the containment portion 201*b* to the body portion 201*a*. The slit 205 mates with and is complementary to tab 209.

Figure 6:
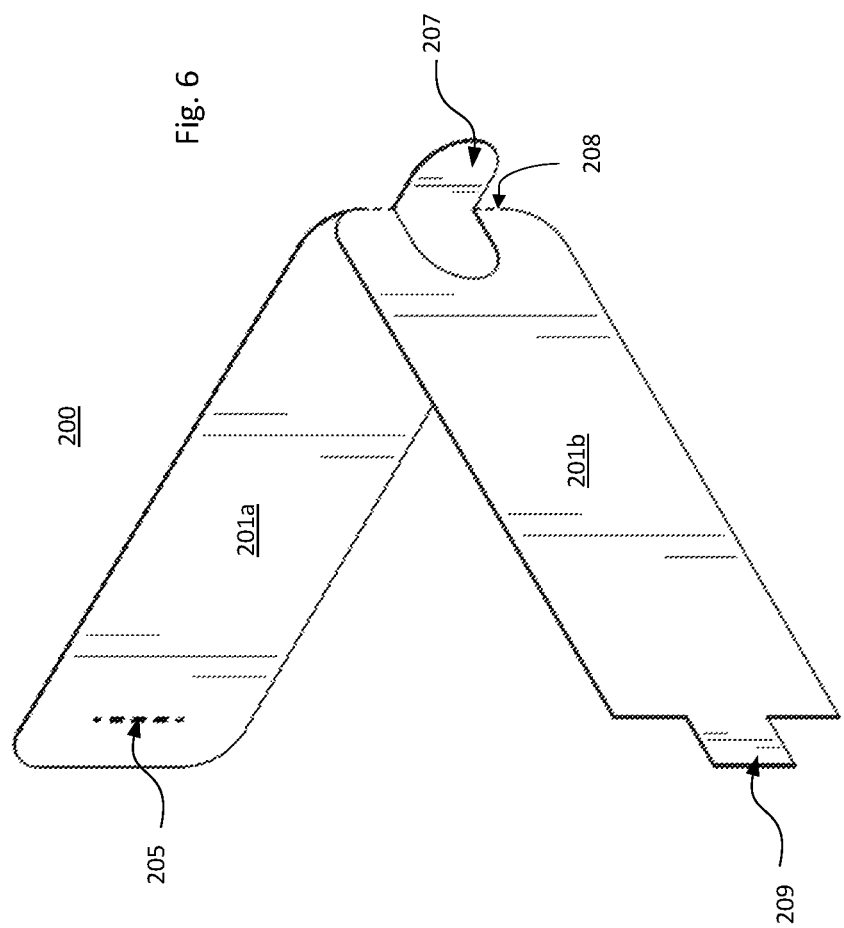
FIG. 6 is an exemplary illustration of the enclosure device of FIG. 5 for delivering an implantable sheet-like repair device in a partially folded state.

FIG. 6 depicts an enclosure device of the invention in a partially folded state. Although the enclosure device is depicted as folding in equal halves, the fold line 208 is not required to be at the center of the planar body and need only be located such that panels 201*a* and 201*b*, when folded, sufficiently capture an implantable sheet-like repair device, allowing for its delivery to a surgical site.

As described herein, the size and dimensions of any enclosure device of the invention, such as length, area, thickness, height of fold, etc. may be varied depending on the type and location of the surgical site and the nature of the implantable sheet-like repair device to be inserted, for example, when the enclosure device is used for implanting a relatively thicker repair device. The use of relatively thicker pads than those described above and also multi-layered support and repair devices are expressly contemplated as embodiments of the invention.

Although not shown in FIGS. 5 and 6, the outer side of one of the panels 201*a* and 201*b* may also include an imprint, coloration, cuts or other markings notifying the user, typically a surgeon, of the side of the enclosure device 200 that should be delivered facing and/or in contact with the body part being repaired, such as a tendon.

Figure 7:
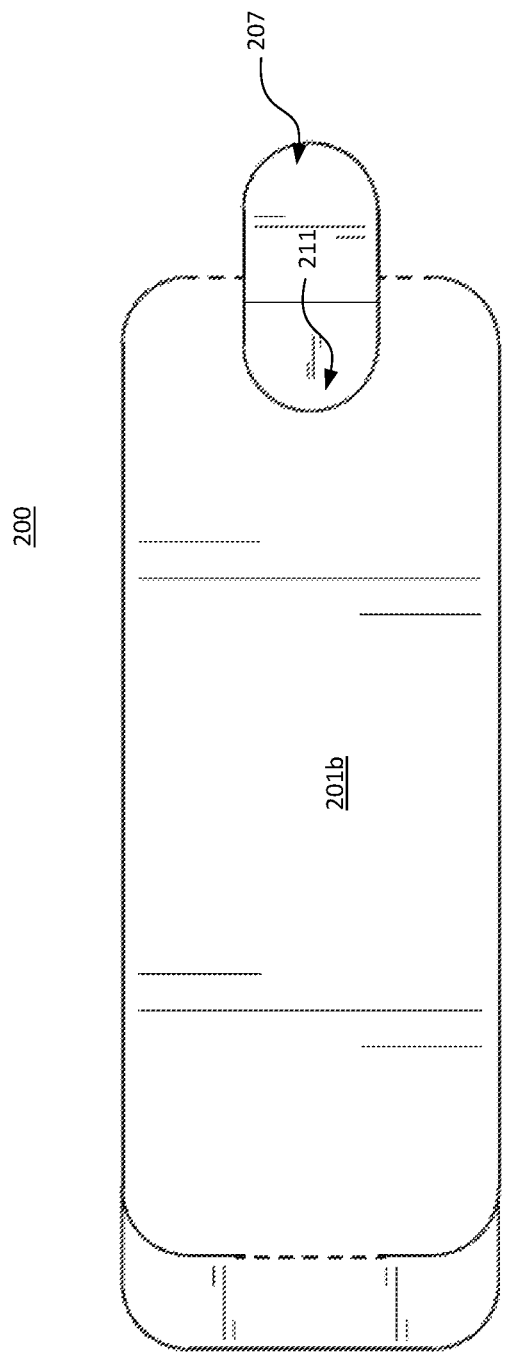
FIG. 7 shows an implantable sheet-like repair device in the enclosure device of FIGS. 5 and 6.
Figure 8:
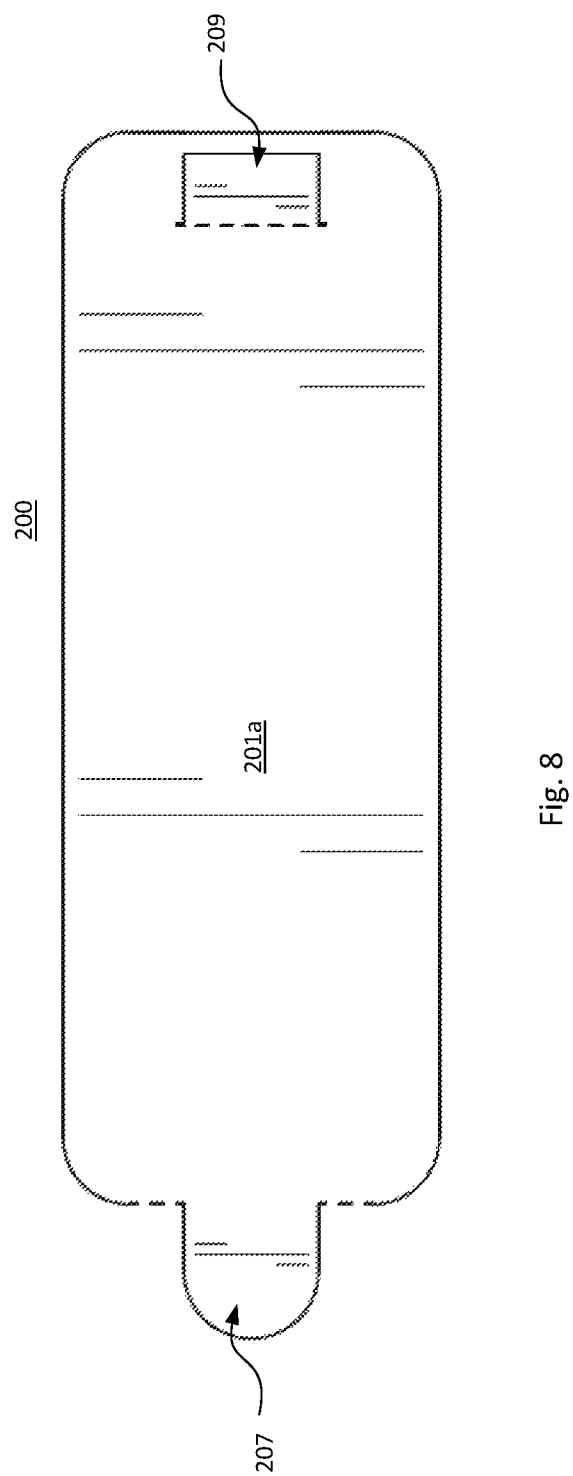
FIG. 8 is an exemplary illustration of a rear view of the enclosure device of FIGS. 5-7 in a fully folded and secured state.

An enclosure device for delivering an implantable sheet-like repair device to a surgical site will be used by a surgeon to contain and protect the sheet-like, tissue repair device. Optionally, an implantable sheet-like repair device will be pre-packaged with the enclosure device for use during surgery. As shown in FIG. 7, such an enclosure device 200 has a planar body folded along a fold line into two panels configured to contain the sheet-like soft tissue repair device 211 between the panels 201*a* and 201*b*. An implantable sheet-like repair device contained between the two panels. As shown in FIG. 7 an enclosure also may have an optional positioning tab 207 extending out from the fold that can be used to pull the enclosure into the intended site at which the repair device is intended to be implanted. The enclosure also may have an optional securing mechanism to secure the enclosure device in a folded position. As shown in FIG. 8 an enclosure using a mated slit and tab securing mechanism, when in a folded and secured position, will have the tab peeking through panel 201*a* containing the slit.

Figure 9:
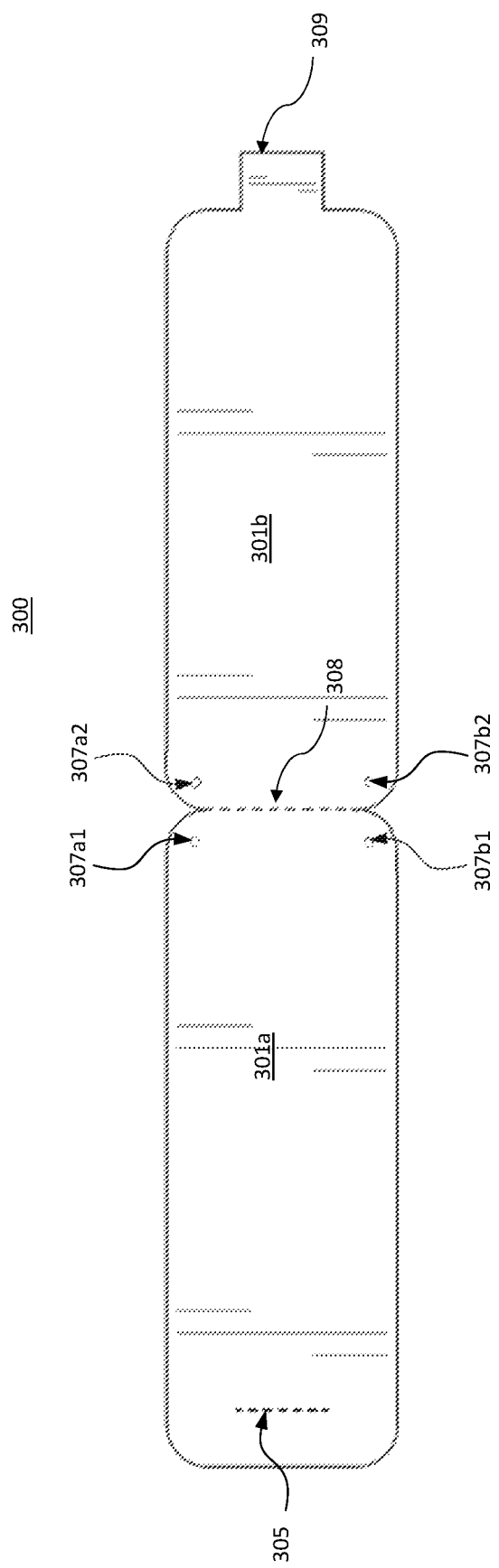
FIG. 9 is an exemplary illustration of another enclosure device of the invention with a suture or filament attachment site for delivering an implantable sheet-like support or repair device to support the repair of injured or damaged soft tissue.
Figure 10:
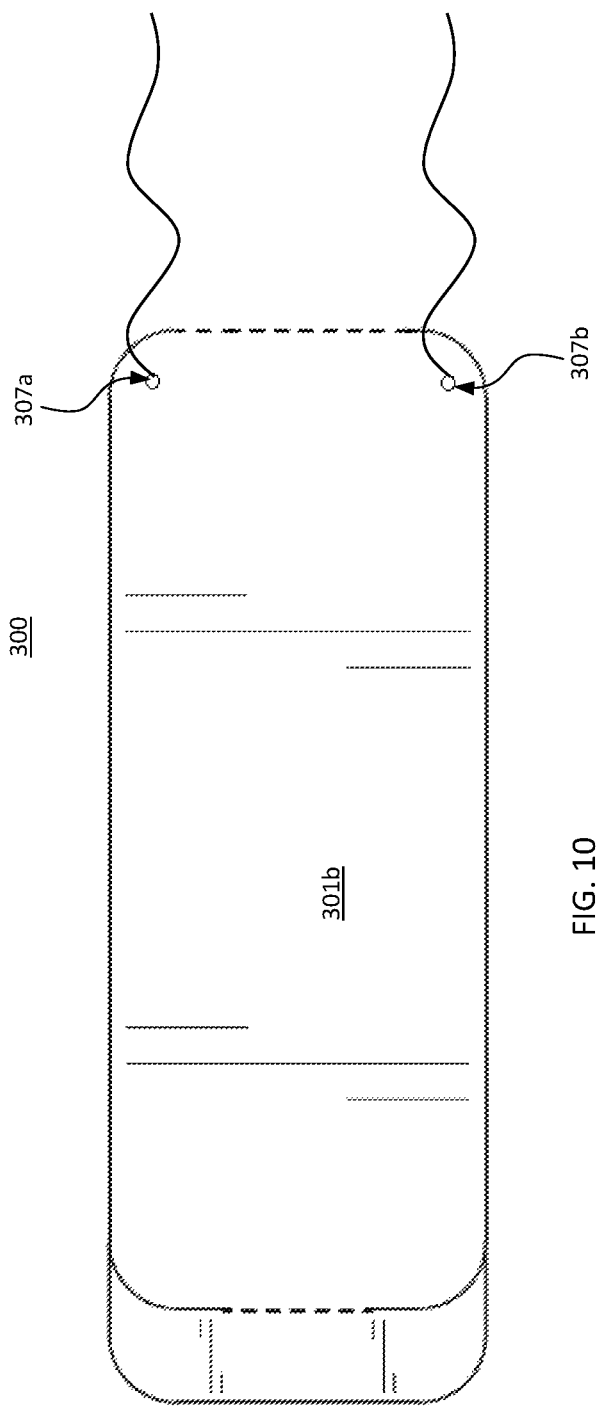
FIG. 10 shows an implantable soft tissue repair device, in the enclosure device of FIG. 9.

FIG. 9 is an exemplary illustration of another enclosure device of the invention using optional suture or filament attachment or connection sites for delivering an implantable sheet-like repair device. In FIGS. 9 and 10, the enclosure device 300 includes a positioning mechanism that includes the body portion 301a having suture or filament attachment sites 307a1 and 307b1 and the containment portion 301b having suture or filament attachment sites 307a2 and 307b2. The suture or filament attachment site 307a1 corresponds with site 307a2 (i.e., corresponding sites 307a) and suture or filament site 307b1 corresponds with site 307b2 (i.e., corresponding sites 307b).

A suture or filament passes through one or both of the corresponding suture attachment sites 307a1 or 307a2 and sites 307b1 or 307b2. The enclosure device 300 suture or filament attachment sites 307a1, 307a2, 307b1, and 307b2 provide a way pull the enclosure device 300 into the intended position for the repair device within the implantation site. Using a suture or filament passed through both corresponding sites optionally facilitates greater control over positioning of the enclosure device 300 without, when pulled, placing strain on the body portion 301a or containment portion 301b separately. Further, using both sets of corresponding sites 307a1 with 307a2 and 307b1 with 307b2 facilitates greater control over positioning of the enclosure device 300 by providing more points of control. Additionally, the sutures or filaments, as seen in FIG. 10, may be pre-attached to sites 307a and 307b before implantation; or a suture or filament may be passed through sites 307a and 307b during a surgical procedure.

Figure 11:
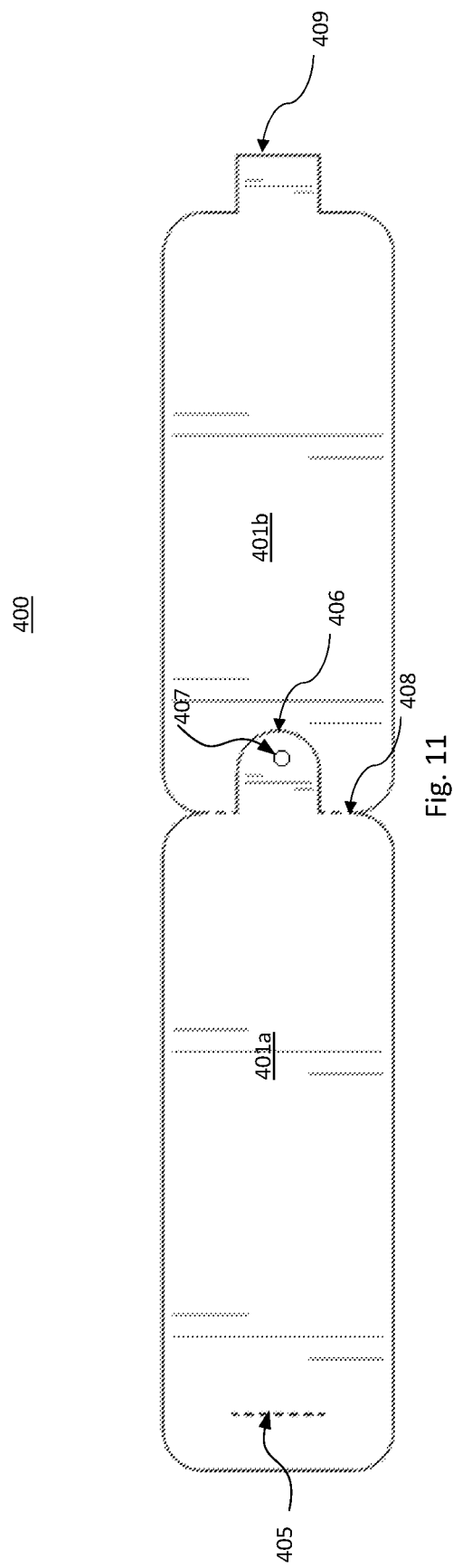
FIG. 11 is an exemplary illustration of another enclosure device of the invention with a suture or filament site on a positioning tab for delivering an implantable sheet-like support or repair device.
Figure 12:
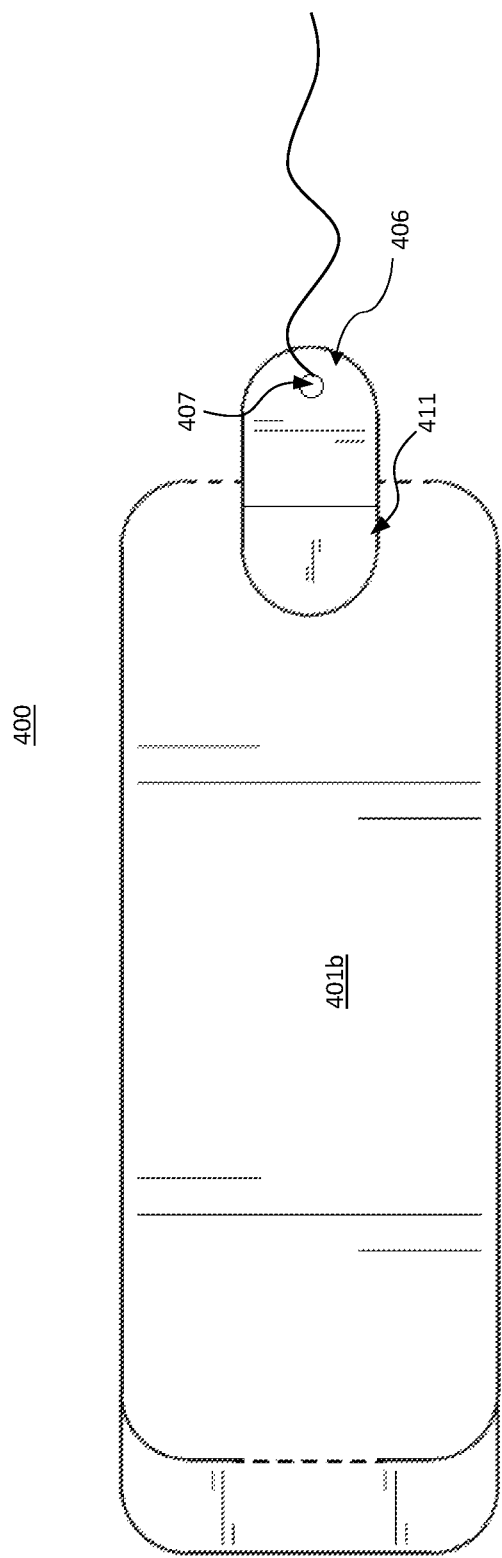
FIG. 12 shows an implantable sheet-like repair device, in the enclosure device of FIG. 11.

Similarly, FIG. 11 is an exemplary illustration of another enclosure device of the invention using an optional suture or filament site on an optional positioning tab for delivering an implantable sheet-like repair device. In FIGS. 11 and 12, the positioning mechanism includes a suture or filament attachment site 407. A suture or filament passes through the site 407 to provide a way to position the enclosure device 400 within the implantation site or attachment position. The enclosure device 400 suture or filament sites provide a way to position the enclosure device 400 within the implantation site or attachment position. The suture or filament, as seen in FIG. 11, may be pre-attached to site 407, or a suture or filament may be passed through 407 during a surgical procedure. To facilitate positioning within an implantation site or attachment position with greater access limitations, the suture or filament site may optionally be included with any positioning tabs of any enclosure devices.

As shown in FIG. 12 an enclosure also may have an optional positioning tab 406 extending out from a fold with suture attachment site 407 through which a suture or filament may be passed to pull the enclosure with enclosed repair device 411 into position for implantation.

In FIGS. 9-10/11-12, the securing mechanism includes a single slit 305/405 and tab 309/409 for securing the containment portion 301b/401b to the body portion 301a/401a. The slit 305/405 mates with and is complementary to tab 309/409 when the enclosure device 300/400 is folded at the fold line 308/408.

Having discussed and shown exemplary embodiments of enclosure devices of the invention with reference to FIGS. 1-12, the general aspects of enclosure devices of the invention are discussed next.

An enclosure device of the invention is configured to contain, transport, position, and remove an implantable sheet-like ligament tendon or other soft tissue support or repair device, from the enclosure device at a surgical site without unwanted deformation or tearing of the repair device and without the repair device adhering to the enclosure device or other tissue in the vicinity of the repair site or between that site and the incision through which the repair device is inserted in a subject. An enclosure device of the invention may be pre-folded to capture the repair device between two planar panels of the enclosure device. Or, a fold-line may be pre-scored to aid in the folding of an enclosure device around a repair device, such as for enclosure devices that are made from a more brittle material or for thicker repair devices. An enclosure device of the invention may include a guide edge (not shown) that may only allow directional access to for separation of the repair device with a particular movement.

An enclosure device captures an implantable sheet-like repair device by folding and may provide means, such as tabs and slots, to secure the folded panels together. In surgical use, an enclosure device containing an implantable sheet-like repair device may then be positioned at the injury site, and the enclosure device readily may be removed from the positioned an implantable sheet-like repair device. The implantable sheet-like repair is then held in place and sutured or adhered to the injury site by conventional techniques for reconstruction, regeneration, and/or therapy at the point of injury, such as injured soft tissue.

For an enclosure device of the invention, the planar body may be formed in any appropriate shape and folded to create the panels, like a clamshell or like a manila document folder found in most business offices. However, the planar body generally will be rectilinear, for example, rectangular or square in shape, when the implant is similarly rectilinear in shape, as is contemplated for the support and repair of damaged ligaments and tendons. In other embodiments, the planar body may have other geometric shapes, such as a triangle, a pentagon, a hexagon, an octagon, a trapezoid, a rhombus, and the like or be irregularly shaped. The corners of the planar body may be squared, angled or rounded. In other embodiments, the planar body may have a non-geometric shape such as a circle, an oval, an egg-shape, and the like. However, when folded, the planar body generally has two panels to capture an implantable sheet-like repair device without extensive overhang by one of the panels.

An enclosure device of the invention optionally includes one or more cutouts in at least one panel of the enclosure device at the end opposite the fold to expose a portion of an implantable sheet-like repair device to facilitate removal of the repair device from inside the enclosure device when positioned by a surgeon at a desired implantation site. Preferably, each panel will have such a cutout so that the repair device can be restrained manually by a surgeon's fingers, by surgical tooling, or by a suture attached at or near to the implant site. The exposed portion of the repair device thereby may be held in position at the implant site while the enclosure device is separated from the repair device and removed from the subject. The cutouts may have different shapes (that is, non-circular shapes) and may be placed along different parts of an enclosure device of the invention.

The panels of an enclosure device may include complementary cut-outs which provide access to the exposed portion of the implantable sheet-like repair device contained within the enclosure device. The location of the cutout(s) may be along any open side of an enclosure device to create the most accessible location and multiple locations for grasping and manipulating an implantable sheet-like repair device based on surgical variables, for example, surgical procedures and surgical site spacing. Suitable cutouts may be, for example, extended half-circle notches cut out along the open edges of the panels. The cutouts may extend from the edge of a panel toward the center of an enclosure device (typically toward the folded side of the enclosure device). The cutouts may be sized to expose greater portions of an implantable sheet-like repair device for grasping and manipulation at the surgical site. When an enclosure device is folded, complimentary cutouts provide unimpeded separation of the enclosure device from the repair device while the repair device is held in position.

An enclosure device of the invention may also include an optional positioning mechanism to position the enclosure device at the support or repair site. The optional positioning mechanism may include a positioning tab, suture or filament attachment site through which a suture or filament may be passed or otherwise attached.

When present, a positioning tab may extend from the fold of an enclosure device providing a mechanism to pull and position the enclosure device through/within small spaces. Typically, a tab will be opposite the cut-out described above. Alternatively, a positioning tab may be located on different parts of the enclosure device based on the surgical variables. The positioning tab may be grasped by the surgeon and used to pull and/or position an enclosure device with an implantable sheet-like repair device in tow within the enclosure device. A positioning tab may be contiguous to the body portion and cut from a panel of the enclosure device. Although generally rounded in shape, a tab may have different shapes/lengths based on surgical site spacing, surgical procedures, accessibility of the surgeon when placed within the surgical site and surgeon hand/finger dimensions (width, length, etc.), to make the positioning tab easier to grasp and manipulate. Further, when present, a suture or filament attachment site may provide a pass through for a suture or filament to be grasped by the surgeon to pull and position the enclosure device through/within relatively constrained spaces at the site of soft tissue repair.

An enclosure device of the invention may also have at least one optional securing mechanism to secure the enclosure device in a folded position. A securing mechanism should not block the removal of a sheet-like, soft tissue repair device from an enclosure device and is preferably releasable to open a folded enclosure device. Suitable securing mechanisms known in the art include, but are not limited to, mated slits and tabs, clasps, crimps, welds, ties, fasteners, snaps, hooks, adhesives/tapes, bands, and the like. Securing mechanisms, for example, the slit(s) and tab(s), are preferably flush and/or smooth along the planar panels of an enclosure device.

The composition and rigidity of an enclosure device may be determined by surgical variables, such as, surgical site space, physical impediments, etc. For example, the material of an enclosure device may be selected to be flexible enough to pass through small spaces, to be rigid enough to protect the repair device, to prevent material leach, to be packaged and sterilized for therapeutic use, and/or to not adhere to an implantable sheet-like soft tissue support or repair device.

An enclosure device of the invention preferably is made of material previously cleared or approved for use in other devices by the Food and Drug Administration (FDA), such as a biocompatible plastic. Suitable materials include, but are not limited to, Acetal, Polyurethane (PUR), Ultra-high-molecular-weight Polyethylene (UHMW-PE), Low-density Polyethylene (LDPE), High-density Polyethylene (HDPE), polylactic acid (PLA), Polyether ether ketone (PEEK), Polyethylene terephtalate (PET), Polytetrafluoroethylene (PTFE or "Teflon"), or Polyvinylidene fluoride (PVDF).

Such materials may have different ideal thicknesses between about 0.0025 mm and about 2 mm, between about 0.05 mm and about 1.5 mm, between about 0.1 mm and about 1 mm, between about 0.2 mm and about 0.8 mm, between about 0.2 mm and about 0.5 mm or between about 0.1 mm and about 0.5 mm. The thickness of the material should allow for folding and may, for example, be about 0.25 mm.

Selection of the material may also be based on surgical requirements and considerations as well as the ability to be sterilized, for example by irradiation using an e-beam in a range, for example from about 25 to 50 kilogray (kGy), prior to packaging and/or surgical use. For example, PTFE and acetal materials may become brittle after irradiation and lose their flexibility. As such, these materials may not be preferable for delivery of the repair device to a surgical site that has small spaces or tight corners. For further example, UHMW-PE and PVDF are not affected by irradiation and thus could be chosen for surgical sites with smaller spaces. Additionally, UHMW-PE is more supple than PVDF, thus depending on the space of the surgical site, a user/surgeon may prefer a more supple flexible device and select UHMW-PE as the material. An enclosure device may be made from a material having the same properties mentioned above and which is also biodegradable in the body without harm. Alternatively, the materials may be sterilized by gamma irradiation, ethylene oxide, plasma, supercritical carbon dioxide, ozone or other available sterilizing treatments that will not substantially change the insert's material properties.

In one embodiment, the thickness of a support and repair device for a damaged or injured Achilles tendon is within a range of about 2.0 to 10 mm before packaging. However, the foldable portion of an enclosure device must be able to account for the thickness of an implantable, sheet-like repair device within the enclosure device. To accommodate different configurations of the sheet-like repair device the height (the distance between the panels) of the folded enclosure may be varied in size or be expandable, such as in a parallel multiple-fold line configuration with fold lines spaced slightly apart from one another. For example, when an implantable, sheet-like repair device is intended for repair of an Achilles tendon and is relatively thicker, the repair device may be folded at two parallel but slightly spaced apart fold lines to include an implant that is between about 5 cm by 7 cm and about 5 cm by 3 cm (the 5 cm length running along the length of the tendon).

Also, most implantable sheet-like repair devices are typically highly compressible. Thus, packaging of an enclosure device containing a sheet-like, soft tissue repair device may compress the repair device a bit. The enclosure device may fold to envelope an Achilles repair device and either flex around the thickness of the repair device or the fold in the enclosure may have a sufficient size to account for the thickness of the enclosed soft tissue repair device.

In surgical use, an enclosure device containing an implantable, sheet-like repair device may then be positioned at the injury site where the device is intended to be implanted, and the enclosure device then may be removed from the positioned sheet-like, soft tissue repair device. The repair device is retained in place and sutured or adhered to the injury site for reconstruction, regeneration, and/or therapy of the injured soft tissue.

An enclosure device of the invention is intended to work with any implantable sheet-like repair device and material or composition known in the art. Preferred implantable sheet-like repair devices include but are limited to sheet-like, soft tissue repair device that may be made from collagen alone or with a biopolymer. Preferred biopolymers include poly-lactic acid (PLA), poly(D-lactic acid)(PDLA), poly(D,L-lactic acid) (PDLLA), poly(lactic-co-glycolic acid) (PLGA), poly(glycolic acid) (PGA) and mixtures thereof. Appropriate biopolymers are described in US Patent Applications 2019/0054205 A1 and 2019/0134267 A1.

The invention also relates to a method of delivering an implantable sheet-like support or repair device to a surgical site using an enclosure device of the invention. A method of the invention positions an enclosure device containing a preferred sheet-like, soft tissue device within a surgical site; separates the enclosure device from the repair device; and implants the repair device at the surgical site. Use of the enclosure device during arthroscopic, minimally invasive and open surgical procedures is contemplated.

Optionally, the enclosure device itself may have suture or filaments passed through sites at one or more sides in order to permit a surgeon to draw the enclosure device into the desired implantation site or attachment position, having the sheet-like support or repair device enclosed.

Figure 13:
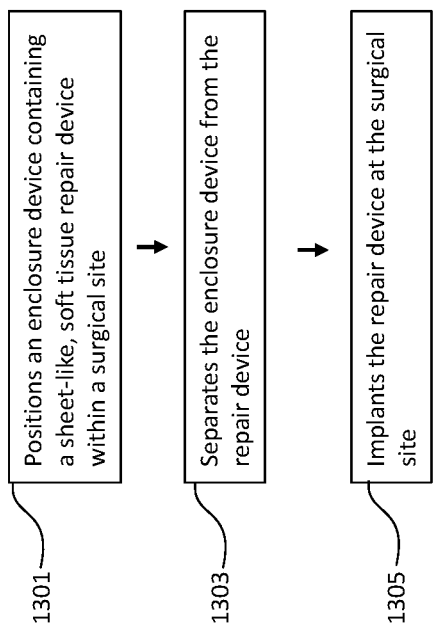
FIG. 13 shows a method of delivering an implantable sheet-like, soft tissue repair device to a surgical site using an enclosure device of the invention.

FIG. 13 is a flow chart for a method according to the invention. Referring to exemplary enclosure devices as shown in FIGS. 1-4/5-8, in step 1301, the enclosure device 100/200 contains an exemplary sheet-like, soft tissue repair device 111/211, and the enclosure device 100/200 may be positioned at a surgical site for implantation of the repair device 111/211. The implantation site may be within a tight space and the repair device 111/211 may require protected transport into the tight space. The positioning tab 107/207 aids and facilitates the positioning of the enclosure device 100/200 by a user grasping the tab 107/207 in the tight space to manipulate, adjust, move, and/or pull the enclosure device 100/200, for example by gliding/sliding along host tissue while protecting the repair device. In one example, an enclosure device 100/200 may be positioned for an Achilles tendon repair. The enclosure device 100/200 may be pulled, for example by a position tab 107/207, under and around the Achilles tendon to position the exemplary sheet-like, soft tissue repair device 111/211 for implantation on the tendon.

In step 1303, the enclosure device 100/200 may be separated from the positioned sheet-like, soft tissue repair device 111/211. In the exemplary embodiment, the sheet-like, soft tissue repair device 111/211 may be held in place by the user throughout the separation process. Panel 101b/201b may be unfastened from panel 101a/201a. Then, while the enclosure device 100/200 remains in a closed, but unsecured state, the sheet-like, soft tissue repair device 111/211 may be held in place by the user via the exposed cutout portion of the enclosure device 100/200. The enclosure device 100/200 may then be separated from the repair device 111/211 by pulling the enclosure device 100/200 from the implant site and discarded or sanitized for reuse.

In step 1305, the sheet-like, soft tissue repair device 111/211 may be implanted at the injury site to reinforce, regenerate, reconstruct, or provide therapeutic effects for the injured soft tissue. The repair device may be fastened to the injury site through sutures, staples, or other acceptable fastening mechanism, for example, glued with a bioadhesive. A sheet-like, soft tissue repair device 111/211 may also be partially adhered to the injury site prior to removal of the enclosure device 100/200. Alternatively, an enclosure device 100/200 may be implanted with the repair device 111/211, for example, by suturing both to the injury site, to further prevent unwanted movement of the repair device 111/211. The enclosure device 100/200 may then be removed through cutting, breaking, or other removal method. Further, an enclosure device 100/200 may, in some instances, where the enclosure device 100 may be reabsorbed in the body without harm, be left implanted with the repair device 111/211.

An enclosure device 100/200 of the invention may also be used to deliver other therapeutic agents to the surgical site along with an implantable sheet-like repair device 111/211. Such therapeutic agents may include, for example, cells, growth factors, platelet-rich plasma (PRP), blood, metallic ions, inhibitors, etc. to introduce additional regenerative factors, as well as, antibiotics, anti-inflammatories, bisphosphonates, and other drugs/medicines to introduce additional reparative factors. Such agents may, for example, be coated onto the enclosure device.

Although the invention has been described with reference to various exemplary embodiments, it is to be understood that these embodiments are merely illustrative of the principles and applications of the invention. Those having skill in the art would recognize that various modifications to the exemplary embodiments may be made, without departing from the scope of the invention. Various features and/or characteristics of differing embodiments of the invention may be combined with one another. Any directional aspects of an enclosure device of the invention as it is described, oriented or appears in the drawings are presented for convenience only; they are not intended to be limiting or to imply that the device has to be used or positioned in any particular orientation.

The claimed invention is:

1. An enclosure device for delivering an implantable sheet-like repair device to a surgical site comprising:
   a planar body foldable along one or more fold lines into at least two panels to contain the implantable sheet-like repair device comprising two planar sides;
   a cutout in one or more panels of the planar body at an open edge of the panel opposite one of the fold lines to expose both planar sides of a portion of the implantable sheet-like repair device;
   a positioning mechanism proximate to a fold line of the enclosure device; and
   a securing mechanism to secure the enclosure device in a folded position.

2. An enclosure device of claim 1, wherein the shape of the enclosure device is substantially rectilinear, such as a rectangle or square.

3. An enclosure device of claim 1, wherein the implantable sheet-like repair device supports the healing or repair of a soft tissue.

4. An enclosure device of claim 3, wherein the sheet-like, soft tissue repair device comprises substantially pure collagen or a mixture of collagen and a biocompatible polymer.

5. An enclosure device of claim 4, wherein the biocompatible polymer is selected from the group consisting of polylactic acid (PLA), poly(D-lactic acid)(PDLA), poly(D,L-lactic acid) (PDLLA), poly(lactic-co-glycolic acid) (PLGA), poly(glycolic acid) (PGA) and mixtures thereof.

6. An enclosure device of claim 1, wherein the enclosure device comprises a material selected from the group consisting of Acetal, Polyurethane (PUR), Ultra-high-molecular-weight Polyethylene (UHMW-PE), Low-density Polyethylene (LDPE), High-density Polyethylene (HDPE), polylactic acid (PLA), Polyether ether ketone (PEEK), Polyethylene terephthalate (PET), Polytetrafluoroethylene (PTFE or "Teflon"), and Polyvinylidene fluoride (PVDF).

7. An enclosure device of claim 1, wherein the securing mechanism comprises a mated tab and slit.

8. An enclosure device of claim 1, wherein the positioning mechanism comprises a positioning tab extending out from one of the fold lines of the enclosure device.

9. An enclosure device of claim 2, wherein the enclosure device comprises a rounded corner when in the folded position.

10. An enclosure device of claim 8, wherein the positioning tab comprises a rounded edge.

11. An enclosure device of claim 1, wherein the positioning mechanism comprises an attachment site to pass a filament through the enclosure device such that manipulating the filament positions the enclosure device.

12. An enclosure device of claim 11, wherein the attachment site is a hole that passes through the enclosure device when in the folded position.

13. An enclosure device of claim of claim 8, wherein the positioning tab comprises an attachment site to pass a filament through the positioning tab such that manipulating the filament positions the enclosure device.

14. An enclosure device of claim 1, wherein the securing mechanism is selected from a group consisting of slits and tabs, clasps, crimps, welds, ties, fasteners, snaps, hooks, adhesives, tapes, and bands.

15. A method of delivering an implantable sheet-like repair device to a surgical site using an enclosure device with a planar body foldable along one or more fold lines into at least two panels to contain the implantable sheet-like repair device comprising two planar sides, a cutout in one or more panels of the planar body at an open edge of the panel opposite one of the fold lines to expose both planar sides of a portion of the implantable sheet-like repair device, and a securing mechanism to secure the enclosure device in a folded position, the method comprising steps of:

positioning, using a positioning mechanism proximate to one of the fold lines of the enclosure device, within the surgical site;

separating the enclosure device from the repair device; and implanting the repair device at the surgical site.

16. A method of claim 15, wherein the positioning step comprises the steps of:

placing the enclosure device at the surgical site, and holding the portion of the repair device exposed through the cutout in the panels to place the repair device within the surgical site.

17. A method of claim 15, wherein the separating step comprises the step of pulling the positioning mechanism to remove the enclosure device, thereby leaving the implantable sheet-like repair device positioned at the surgical site.

18. A method of claim 15, wherein the implantable sheet-like repair device is a sheet-like, soft tissue repair device.

19. A method of claim 18, wherein the sheet-like, soft tissue repair device comprises collagen or a mixture of collagen and a biocompatible polymer.

20. A method of claim 18, wherein the biocompatible polymer is selected from the group consisting of polylactic acid (PLA), poly(D-lactic acid)(PDLA), poly(D,L-lactic acid) (PDLLA), poly(lactic-co-glycolic acid) (PLGA), poly (glycolic acid) (PGA) and mixtures thereof.

21. A method of claim 15, wherein the enclosure device comprises a material selected from the group consisting of Acetal, Polyurethane (PUR), Ultra-high-molecular-weight Polyethylene (UHMW-PE), Low-density Polyethylene (LDPE), High-density Polyethylene (HDPE), polylactic acid (PLA), Polyether ether ketone (PEEK), Polyethylene terephthalate (PET), Polytetrafluoroethylene (PTFE or "Teflon"), and Polyvinylidene fluoride (PVDF).

22. A method of claim 15, wherein the securing mechanism comprises a mated tab and slit.

23. A method of claim 15, wherein the positioning mechanism comprises a positioning tab extending out from one of the fold lines of the enclosure device.

\* \* \* \* \*